United States Patent [19]

Cros et al.

[11] Patent Number: 5,510,084
[45] Date of Patent: Apr. 23, 1996

[54] PROCESS FOR IMMOBILIZING A NUCLEIC ACID FRAGMENT BY PASSIVE ATTACHMENT TO A SOLID SUBSTRATE, THE SOLID SUBSTRATE THUS OBTAINED, AND ITS USE

[75] Inventors: Philippe Cros, Lyons; Patrice A. Allibert, Grezieu la Varenne; Bernard F. Mandrand, Villeurbanne; Pascal T. Dalbon, Venissieux, all of France

[73] Assignee: Bio Merieux, Marcy l'Etoile, France

[21] Appl. No.: 273,776

[22] Filed: Jul. 12, 1994

Related U.S. Application Data

[63] Continuation of Ser. No. 913,953, Jul. 17, 1992, abandoned.

[30] Foreign Application Priority Data

Jul. 17, 1991 [FR] France .................. 91 09057

[51] Int. Cl.⁶ .............................. G01N 33/48; B01L 9/00
[52] U.S. Cl. .................. 422/104; 435/6; 436/94
[58] Field of Search .................. 435/6; 436/94, 436/8, 807; 536/24.3, 25.4; 935/78; 422/50, 68.1, 99, 104

[56] References Cited

U.S. PATENT DOCUMENTS

| | | | |
|---|---|---|---|
| 4,379,843 | 4/1983 | Cashion | 435/178 |
| 4,739,044 | 4/1988 | Stabinsky | 536/27 |
| 4,828,979 | 5/1989 | Klevan et al. | 435/6 |
| 4,948,882 | 8/1990 | Ruth | 536/27 |
| 4,994,373 | 2/1991 | Stavrianopoulos et al. | 435/6 |
| 5,112,734 | 5/1992 | Kramer et al. | 435/6 |
| 5,138,045 | 8/1992 | Cook et al. | 536/27 |
| 5,185,439 | 2/1993 | Arnold, Jr. et al. | 536/24.3 |
| 5,232,829 | 8/1993 | Longiaru et al. | 435/6 |

FOREIGN PATENT DOCUMENTS

| | | |
|---|---|---|
| 0221308 | 5/1987 | European Pat. Off. . |
| 0435150 | 7/1991 | European Pat. Off. . |
| WO88/01302 | 2/1988 | WIPO . |
| WO89/03849 | 5/1989 | WIPO . |
| WO91/00288 | 1/1991 | WIPO . |
| WO91/08307 | 6/1991 | WIPO . |
| WO91/19812 | 12/1991 | WIPO . |
| WO91/19729 | 12/1991 | WIPO . |

OTHER PUBLICATIONS

M. Zouali et al, "A Rapid ELISA for Measurement of Antibodies to Nucleic Acid Antigens Using UV–treated Polystyrene Plates", *Journal of Immunological Methods*, vol. 90, 1986, pp. 105–110.

R. L. Rubin et al, "An Improved ELISA for Anti–Native DNA by Elimination of Interference by Anti–Histone Antibodies", *Journal of Immunoligical Methods*, vol. 63, No. 3, 1983, pp. 359–366.

Dunn et al, "A Novel Method to Map Transcripts: Evidence for Homology Between An Adenovirus mRNA and Discrete Multiple Regions of the Viral Genome", *Cell*, vol. 12, 23–36, Sep., 1992.

Saiki et al, "Genetic Analysis of Amplified DNA with Immobilized Sequence–Specific Oligonucleotide Probes", *Proc. Natl. Acad. Sci. USA*, vol. 86, pp. 6230–6234, Aug., 1989.

Ranki et al, "Sandwich Hybridization As A Convenient Method for the Detection of Nucleic Acids in Crude Samples", *Gene*, 21, 1983, pp. 77–85.

Palva et al, "Detection of Chlamydia Trachomatis by Nucleic Acid Sandwich Hybridization", *FEMS Microbiology Letters*, 23, 1984, pp. 83–89.

Polsky–Cynkin et al, "Use of DNA Immobilized on Plastic and Agarose Supports to Detect DNA by Sandwich Hybridization", *Clinical Chemistry*, vol. 31, No. 9, 1985, pp. 1438–1443.

Kremsky et al., *Nucleic Acids Res.* 15(7), 2891–2909 (1987).

Zendegui et al., *Nucleic Acids Res.*, 20(2), 307–314 (1992).

*Primary Examiner*—W. Gary Jones
*Assistant Examiner*—Kenneth R. Horlick
*Attorney, Agent, or Firm*—Oliff & Berridge

[57] ABSTRACT

In a process for immobilization by passive fixation on a solid support of a nucleic acid fragment containing less than 100 nucleotides, the fragment is deposited on the support in the form of a derivative. The derivative results from the covalent coupling of the fragment with a ligand having a molecular mass of less than 5,000 and containing at least one polar functional group. The derivative is not capable of forming a covalent bond with the support under the conditions of the deposition. When the ligand is a nucleotide or an oligonucleotide it is at least one nucleotide modified so as to introduce the polar functional group.

20 Claims, 4 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

```
Lys  Ile  Glu  Pro  Leu  Gly  Val  Ala  Pro  Thr  Lys  Ala  Lys  Arg  Arg  Trp
1                  5                        10                       15

Gln  Arg  Glu  Lys  Arg
                20
```

( 2 ) INFORMATION FOR SEQ ID NO:2:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:2:

```
Lys  Gly  Ser  Lys  Gly  Ser  Lys  Gly  Ser  Lys  Gly  Ser  Lys  Gly  Ser  Lys
1                  5                        10                       15

Gly  Ser  Lys  Gly  Ser  Lys  Gly  Ser  Lys  Gly  Ser  Lys  Gly  Gly
                20                       25                       30
```

( 2 ) INFORMATION FOR SEQ ID NO:3:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GCATTTAGAG CC                12

( 2 ) INFORMATION FOR SEQ ID NO:4:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:4:

TGCATTTAGA GCC                                                                                          13

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:5:

TCTACGCATT TCACCGCTAC AC                                                                                22

(2) INFORMATION FOR SEQ ID NO:6:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:6:

AAGGTCAACC GGAATTTCAT TTTGGGGCTC TAAATGCAAT ACAATGTCTT GCAATGTTGC        60

CTTA                                                                                                    64

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:7:

TAAGGCAACA TTGCAAGATA                                                                                   20

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

TCTAATCCTG TTTGCTCCC　　　　　　　　　　　　　　　　　　　　　　　　　　　　19

( 2 ) INFORMATION FOR SEQ ID NO:9:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:9:

ATTCCGTTGT AACGTTCTGT AACATAACGT AAATCTCGGG GTTTTACTTT AAGGCCAACT　　　60

GAA　　　　　　　　　　　　　　　　　　　　　　　　　　　　　　　　　　　　63

( 2 ) INFORMATION FOR SEQ ID NO:10:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

ATTCCGTTGT AACGTTCTGT AACATAACGT AAGTCTCGGG GTTTTACTTT AAGGCCAACT　　　60

GAA　　　　　　　　　　　　　　　　　　　　　　　　　　　　　　　　　　　　63

( 2 ) INFORMATION FOR SEQ ID NO:11:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

GACAACTGAT CTCTAC　　　　　　　　　　　　　　　　　　　　　　　　　　　　　16

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (iv) ANTI-SENSE: NO (xi) SEQUENCE DESCRIPTION: SEQ ID NO:12:

CCGGACAGAG CCCATTAC                    18

PROCESS FOR IMMOBILIZING A NUCLEIC ACID FRAGMENT BY PASSIVE ATTACHMENT TO A SOLID SUBSTRATE, THE SOLID SUBSTRATE THUS OBTAINED, AND ITS USE

This is a continuation of application Ser. No. 07/913,953 filed Jul. 17, 1992, now abandoned.

The present invention relates to a process for the immobilization of a nucleic acid fragment on a solid support, the solid support thus obtained and its use, in particular in methods for the detection of target sequences containing a sequence complementary to the immobilized sequence.

It is known that one of the properties of nucleic acids is the possibility of interacting with a complementary sequence via hydrogen bonds and of forming a hybrid in accordance with the known pairing laws, that is to say A-T, G-C for DNA and A-U, G-C for RNA.

On the basis of the properties of nucleic acids, techniques have been developed which make it possible to demonstrate and to quantify, in a sample to be analyzed, a nucleic acid designated the target nucleic acid. These techniques may be divided into two large groups: the techniques termed direct detection techniques, such as those developed by SOUTHERN. E. M. (J. Mol. Biol., 98, 503, (1975)) and the technique known as "dot-blot" (MANIATIS et al., Molecular Cloning, Cold Spring Harbor, (1982)) for the detection of DNA, according to which techniques the target (DNA) is deposited on a film of nitrocellulose, nylon or a mixture of nitrocellulose and nylon and a predetermined nucleic sequence, termed the detection probe, labeled by any known label such as an enzyme, chemical or radioactive label, is used for detection. Thus, when the nucleic sequence of the target and the nucleic sequence of the detection probe are complementary, a stable hybrid forms and, following a washing step in order to remove the non-paired detection probe, it is possible to quantify the target in the sample. Another direct detection technique is the technique known as the "NORTHERN" technique, which in practice is identical to the technique known as the "SOUTHERN" technique but is used to demonstrate and quantify ribonucleic acid. The techniques known as indirect techniques, such as the sandwich or "reverse dot" technique, are a modification of these techniques. According to said "reverse dot" technique, a first nucleotide probe, termed the capture probe, fixed on a solid support is used, which serves to capture the gene or gene fragment to be detected in the sample. The target may have been labeled beforehand (most often by a hapten or by a chemical modification). In this case, an appropriate detection will be carried out. If the target is not labeled, a second probe, termed the detection probe, which is complementary to another region of the target, may then be added, which permits detection via a label such as a radioactive, enzymatic or chemical label (see, for example, DUNN A. R. and HASSEL J. A, Cell, 12, pp. 23–36 (1977); RANKI M. et al., Gene, 21, pp. 77–85 (1983); PALVA A. et al., FEMS Microbiol. Lett. 23, pp. 83–89 (1984); POLSKY-CYNKI R. et al., Clin. Chem., 31, pp. 1438–1443 (1985)).

All of these techniques necessitate the immobilization of a nucleic acid fragment on a solid support. The method most commonly used to bind a nucleic acid fragment to a support is to attach said fragment by diverse non-covalent interactions. The disadvantages of this method lie in the fact that one part of the nucleic acid is directly immobilized on the support and that only a small part of the nucleic acid fragment remains available for hybridization. These disadvantages are amplified when relatively short nucleic acid fragments, for example of less than 100 nucleotides (especially less than 50 nucleotides and in particular less than 30 nucleotides), are used. This problem arises in particular when it is desired to detect genetic mutations and polymorphisms. For this purpose synthetic nucleic probes are used which contain about 15 to 20 nucleotides which will hybridize with the targets to be detected only if there is perfect complementarity. In the majority of cases, the mispairing of a single base pair is sufficient to prevent the formation of a stable probe/target complex, under pre-chosen conditions.

Solutions have been proposed to overcome these disadvantages, which solutions include that specified in particular by SAIKI R.K. et al., Proc. Natl. Acad. Sci. USA, vol. 86, pp. 6230–6234, August 1989, which consists in coupling a 400 base poly(dT) tail to the 3' end of an oligonucleotide or probe and in immobilizing the oligonucleotide by means of this poly(dT) tail on a nylon filter by exposure to ultraviolet radiation, so as to effect covalent coupling of the thymine bases to the primary amines present in the nylon.

However, this solution is not entirely satisfactory because it presents specificity problems. In fact, the thymine bases of the oligonucleotide may also react, under UV radiation, with the support, which involves a reduction in the hybridization efficiency. This problem is partially resolved, as described in the publication, by the use of a very long tail (400 bases) but the probe, in mass, then becomes very much smaller than the tail, which accordingly reduces the degree of grafting in moles/g of paper. Moreover, the production of a probe with a tail of such large size poses industrialization problems.

Another solution advocated is that described in Patent Application WO 88/01302, which consists in coupling a ligand, such as an aminoalkyl, to the terminal end of an oligonucleotide and in attaching the free end of this ligand to a solid support, such as polystyrene or the like, by formation of a covalent bond. Although this method makes it possible to ensure stable fixation of the oligonucleotide, it is no less difficult to implement industrially because it requires a support activation step in order to create on the surface of the latter a predetermined reactive group capable of forming a covalent bond with the reactive group carried at the end of the ligand.

A new process has now been found which overcomes the disadvantages mentioned above, which is simple to implement and which ensures excellent reproducibility.

The subject of the present invention is a process for immobilization by passive fixation, on a solid support, of a nucleic acid fragment containing less than 100 nucleotides (especially less than 50 nucleotides and in particular less than 30 nucleotides), in which process said fragment is deposited on said support in the form of a derivative resulting from the covalent coupling of said fragment with a ligand having a molecular mass of less than 5000 and containing at least one polar functional group, said derivative not being capable of reacting with said support with the formation of a covalent bond under the conditions of said deposition, it being understood that when said ligand is a nucleotide or oligonucleotide it comprises at least one nucleotide modified so as to introduce said polar functional group.

"Passive fixation" is understood to be a fixation due to forces other than covalent bonding forces.

In particular embodiments, the process of the invention may also have the following characteristics, taken on their own or, if necessary, in combination:

said functional group is chosen from amine, amido thiocarboxyl, hydrazino, hydrazono, imino, azido, triazeno, triazano, optionally substituted amide, semicarbazono, carbamoyl, cyano, carboxyl, hydroxyl, alkylthio, arylthio, sulfamoyl and thiophosphate groups;

said polar functional group is chosen from (primary, secondary or tertiary) amine, hydroxyl, alkylthio, amido, carbamoyl, thiocarboxyl, and arylthio groups;

said amine group is chosen from amino, monosubstituted or disubstituted amino (the substituent or substituents being chosen from optionally substituted alkyl or aryl groups), amidino, guanidino, triazinyl, indolyl and imidazolyl groups;

said ligand contains at least one hydrophobic group; said hydrophobic group is chosen, in particular, from optionally unsaturated hydrocarbon groups having from 2 to 30 carbon atoms; the hydrocarbon group or groups may be chosen in particular from alkyl, alkylene, alkenyl and alkenylene groups, aryl and arylene groups and alkyl, alkylene, alkenyl or alkenylene groups, which are optionally interrupted or substituted by at least one arylene or aryl group; the hydrophobic group or groups may be substituted by said polar functional group or groups;

the ligand is preferably bonded to a terminal nucleotide of the immobilized sequence, in particular at the 3' and 5' end of said sequence, or bonded to the base (thymine, cytosine, etc.) of said terminal nucleotide; the ligand may also be bonded to a non-terminal nucleotide base or to the phosphorus of an intranucleotide bond;

said ligand contains a group chosen from:

the groups of formula (I):

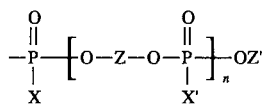

in which n is zero or an integer from 1 to 30, the groups Z are chosen from alkylene or alkenylene groups having 2 to 30 carbon atoms, Z' is an alkyl or alkenyl-group having 2 to 30 carbon atoms and X and X' independently represent —O$^-$M$^+$, —S$^-$M$^+$ or an alkyl, alkoxy, aryloxy, aminoalkyl or aminoalkoxy group, M$^+$ being an alkali metal cation or NH$_4^+$, it being understood that at least one of the groups Z and/or Z' is substituted by a polar functional group or by a group carrying a polar functional group;

the groups of formula (II):

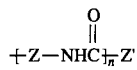

in which n, Z and Z' are defined as above, and the groups of formula (III):

 (III)

in which L is a peptidyl radical, the free valency of which is bonded, for example, to the N-terminal or C-terminal end, said peptidyl radical comprising at least one unit derived from an amino acid containing a side chain substituted by a polar functional group;

said ligand corresponds to the formula (I), n being zero or an integer from 1 to 10, Z is an alkylene having from 2 to 12 carbon atoms and Z' is an alkyl having from 2 to 12 carbon atoms, at least one of the groups Z and Z' being substituted by at least one amine, hydroxyl or hydrazino group; in particular, n=0 and X represents O$^-$M$^+$;

said ligand corresponds to the formula (II) where n=0 and Z' represents an alkyl group having 3 to 12 carbon atoms, substituted by at least one amine group; said alkyl group is also substituted by at least one hydroxyl group;

said ligand corresponds to the formula (II) where n=1, Z represents an alkylene having at least two carbon atoms and Z' represents an alkyl group substituted by at least one amine group;

said ligand corresponds to the formula (III) and said amino acid containing a substituted side chain is chosen from lysine, arginine, ornithine, glutamine, asparagine, serine, threonine, tyrosine, histidine and tryptophan.

The compound of general formula (III) is, for example, a peptide such as represented, respectively, by the sequences:
(KGS)$_m$-KGG, m being an integer which may vary from 1 to 15, and
KIEPLGVAPTKAKRRWQREKR (SEQ ID NO. 1)

The term "nucleic acid fragment" as used in the present invention signifies a natural DNA or RNA fragment or a natural or synthetic oligonucleotide or a synthetic DNA or RNA fragment which is non-modified or contains one or more modified bases such as inosine, 5-methyldesoxycytidine, 5-dimethylaminodesoxyuridine, desoxyuridine, 2,6-diaminopurine, 5-bromodesoxyuridine or any other modified base allowing hybridization, it being possible for the nucleic acid fragment to be single-strand or double-strand.

The term "solid support" as used here includes all the materials on which a nucleic acid fragment may be immobilized for use in diagnostic tests, in affinity chromatography and in separation processes. Natural or synthetic materials, which may or may not be chemically modified, may be used as solid support, in particular polysaccharides such as cellulose materials, for example paper, cellulose derivatives, such as cellulose acetate and nitrocellulose; polymers, such as polyvinyl chloride, polyethylene, polystyrenes or polyacrylate, or copolymers, such as vinyl chloride/propylene polymer or vinyl chloride/vinyl acetate polymer; copolymers based on styrenes; natural fibers, such as cotton, and synthetic fibers, such as nylon. The support can be modified by irradiation.

Preferably, the solid support used in the present invention is a polystyrene polymer, a butadiene-styrene copolymer or a butadiene-styrene copolymer in the form of a mixture with one or more polymers or copolymers chosen from polystyrene, styrene/acrylonitrile copolymers or styrene/methyl methacrylate copolymers, polypropylenes, polycarbonate or the like. Advantageously, the support of the present invention is a polystyrene or a styrene-based copolymer containing between about 10 and 90% by weight of styrene units.

The solid support according to the invention may be, without limitation, in the form of a microtitration plate, a sheet, a cone, a tube, a well, beads or the like.

The term "coupling agent" as used here denotes a molecule containing at least two reactive "ends" or groups. The coupling agent may be homobifunctional or heterobifunctional.

The ligands used in the present invention, and given here by way of example, may be commercially available compounds or compounds synthesized by methods known per se.

The invention also relates to a support on which a nucleic acid fragment (as defined above) is immobilized by passive fixation, said support being characterized in that it may be obtained by the process described above. Such a support may be used, in particular, in diverse techniques, such as those of diagnostic tests and those of affinity chromatography. The invention also relates to the use of such a support in a process for the detection or purification, by known techniques, of a nucleotide target containing a sequence complementary to that of the immobilized nucleic acid fragment: in particular, this immobilized fragment may be used as capture probe.

Figure 1:
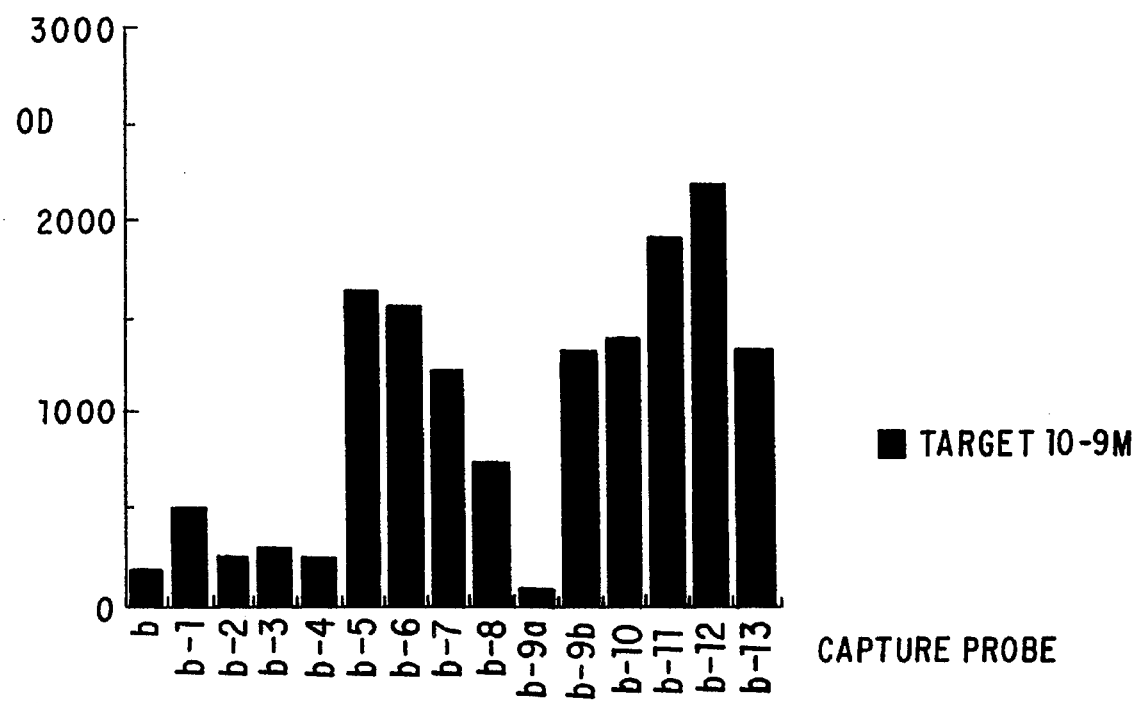
FIG. 1 shows capture oligonucleotides as defined in Tables 4 and 5.

The following examples illustrate the invention without, however, restricting it.

EXAMPLE 1

Phosphoramidite Ligands

The commercially available compounds used in the present invention are listed in Table 1 below

TABLE 1

| No. | Formula | Supplier | ref |
|---|---|---|---|
| 5 | $CF_3-C(=O)-NH-(CH_2)_6-OP(OCH_3)(N(isoPr)_2)$ | Applied Biosystems | 400808 |
| 6 | $MMTr-NH-(CH_2)_{12}-O-P(O-(CH_2)_2-CN)(N(isoPr)_2)$ | Clontech Lab Inc | 5206-1 |
| 7 | $MMTr-NH-(CH_2)_3-O-P(O-(CH_2)_2-CN)(N(isoPr)_2)$ | GlenResearch | 10-1903 |
| 8 | $(Ph)_3-C-S-(CH_2)_6-O-P(O-(CH_2)_2-CN)(N(isoPr)_2)$ | Clontech Lab Inc | 5211-1 |
| 9a | $DMTr-O-(CH_2)_2-SO-(CH_2)_2-O-P(O-(CH_2)_2-CN)(N(isoPr)_2)$ | Clontech Lab Inc. | 5210-1 |
| 10 | $Fmoc-NH-CH_2-CH(O-P(O-(CH_2)_2-CN)(N(isoPr)_2))-CH_2-O-DMTr$ | Clontech Lab Inc. | 5203-3 |
| 11 | (DMTrO-deoxyribose nucleoside with 5-substituted pyrimidine bearing $-CH=CH-CH_2-NH-(CH_2)_6-NH-C(=O)-CF_3$, 3'-O-P(O-(CH_2)_2-CN)(N(isoPr)_2)) | GlenResearch | 101039 |

TABLE 1-continued

| No. | Formula | Supplier | ref |
|---|---|---|---|
| 12 | 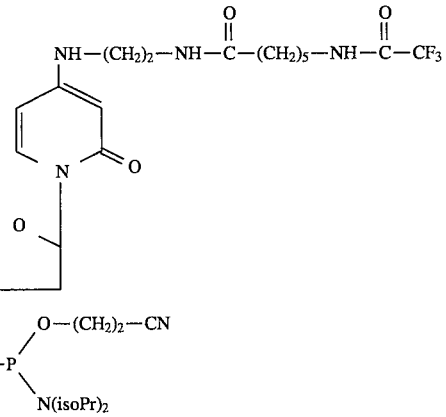 | Cytolab | 2599-01 |
| 13 | CPG—LCAA—O—CH$_2$—CH—CH$_2$—ODMTr<br>　　　　　　　　　　　　｜<br>　　　　　　　　　　　CH$_2$—NH-Fmoc | Clontech Lab Inc | 5221-1 |

DMTr = dimethoxytrityl
MMTr = monomethoxytrityl
Fmoc = fluorenyl-9-methoxycarbonyl
CPG = controlled pore glass
LCAA = long chain alkylamine (spacer arm)

Other phosphoramidite ligands prepared by the Applicant are, respectively, synthesized in accordance with the procedures described below:

a) 2 g of 1,8-octanediol (marketed by ALDRICH 0-330-3), 0.084 g of 4-dimethylaminopyridine and 1.9 ml of triethylamine in 20 ml of anhydrous pyridine are mixed in a 100 ml round-bottomed flask purged with argon. 3 g of 4,4'-dimethoxytriphenylmethyl chloride in 15 ml of pyridine are then added in the course of 30 min. After a reaction time of 1 hour, with stirring, the reaction is blocked by 10 ml of methanol. After extraction with a mixture of ethyl acetate and 0.1M sodium phosphate buffer of pH 7, the organic phase is dried over sodium sulfate and then purified on a silica column using a mixture of CH$_2$Cl$_2$/methanol/triethylamine in the following proportions: 98/1/1.

The fractions containing a product which has a retention factor (Rf) of 0.47 are mixed and concentrated under vacuum. 0.7 g of this dried product are dissolved in 4 ml of anhydrous CH$_3$CN with 4.7 ml of 0.5M tetrazole in CH$_3$CN. The solution is added dropwise to 0.5 g of 2-cyanoethyl-N,N,N',N'-tetraisopropylphosphorodiamidite (marketed by ALDRICH under the reference 30,599-5) in 6 ml of CH$_3$CN.

After a reaction time of 30 minutes, the organic phase is centrifuged. The supernatant is purified by thin layer chromatography on a silica column using a mixture A consisting of hexane/ethyl acetate/triethylamine in proportions of 60/35/5 respectively. The solutions containing the desired product are pooled and concentrated.

The compound obtained is compound referenced 1 represented by the general formula IV below, in which DMTr represents dimethoxytrityl.

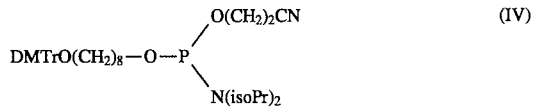

(IV)

The $^{31}$P NMR (nuclear magnetic resonance) chemical shift of compound 1 is 148.40 ppm and its retention factor (Rf) in mixture A is 0.77. The NMR chemical shifts are given with respect to 85% H$_3$PO$_4$.

b) 210 mg of anhydrous 2-benzyloxyethanol (marketed by ALDRICH under the reference 25286-7) in 10 ml of 0.25M tetrazole in CH$_3$CN are added dropwise to 3 ml of CH$_3$CN containing 600 mg of 2-cyano-N,N,N',N'-tetraisopropylphosphorodiamidite.

After a reaction time of 1 hour, with stirring, and with centrifuging to remove the precipitate, the organic phase is concentrated and purified by thin layer chromatography on a silica column using a mixture B of hexane/ethyl acetate/triethylamine in proportions of 50/45/5 respectively.

The compound obtained is compound referenced 2 represented by the general formula V below.

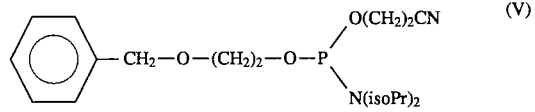

(V)

The characteristics of compound 2 are as follows: $^{31}$P NMR (ppm)=148.57, Rf=0.85 in mixture B. The NMR chemical shifts are given with respect to 85% H$_3$PO$_4$.

c) A procedure identical to that described for the synthesis of compound 2 is used, using 6-phenyl-1-hexanol (marketed by ALDRICH under the reference 33361- 1) as starting material.

After a reaction time of 1 hour, with stirring, and centrifuging to remove the precipitate, the organic phase is concentrated and purified by thin layer chromatography on a silica column using a mixture C consisting of hexane/ethyl acetate/triethylamine in proportions of 70/25/5 respectively.

The compound obtained is compound referenced 3 represented by the general formula VI below:

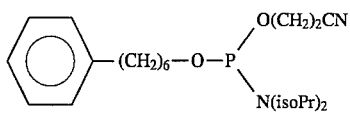
$$\text{(VI)}$$

The characteristics of compound 3 are as follows: $^{31}$P NMR (ppm)=148.40, Rf=0.70 in mixture C.

d) A synthesis procedure identical to that described for compound 2 is used, using 1-hexanol (marketed by ALDRICH under the reference H 1330-3) as starting material. The reaction is not followed by thin layer chromatography, but by $^{31}$P NMR. The reaction is stopped after the starting bisphosphoramidite has disappeared ($\delta^{31}$P=128.18 ppm). The compound obtained is compound reference 4 represented by general formula VII below and is used as the crude product after filtering through 0.45 μm Millex (trade name).

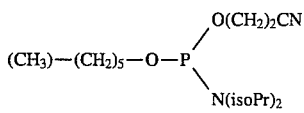
$$\text{(VII)}$$

The $^{31}$P NMR chemical shift is 148.37 ppm.

e) A synthesis procedure identical to that described for compound 2 is used, using 3-dimethylamino 1-propanol (marketed by ALDRICH under the reference D14440-1) as starting material.

The reaction is not followed by thin layer chromatography, but by $^{31}$P NMR. The reaction is stopped after the starting bisphosphoramite has disappeared ($\delta^{31}$P 128.18 ppm). The compound obtained is used as the crude product after filtering through 0.45 μm Millex (trade name).

f) A synthesis procedure identical to that described for compound 2 is used, using as starting material a N-methyl aminoalcohol such as 2-(methylamino) ethanol (marketed by ALDRICH under the reference 23966-6).

EXAMPLE 2

Synthesis of a Thiophosphate Arm at the 5' End of the Oligonucleotide

A solution of 15.02 g of 3-hydroxyproprionitrile (10 992-4 Aldrich) in 40 ml of anhydrous THF and 26 ml of N,N'-diisopropylethylamine (Aldrich D 12580-6) is cooled to −10° C. 10.10 g of dichloro(diisopropylamine)phosphine are added, with stirring, in the course of 30 min. After reaction for a further 20 min, the hydrochloride is filtered off under an inert atmosphere. The filtrate, diluted in 1 liter of ethyl acetate, is extracted 3 times with 150 ml of phosphate buffer of pH 7.00 and then dried over Na$_2$SO$_4$. After concentration under vacuum, the product is purified over silica in the presence of triethylamine.

The compound obtained is compound reference 9b represented by the formula VIII below.

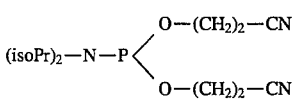
$$\text{(VIII)}$$

EXAMPLE 3

Peptide Ligands

The peptides are synthesized on a phenylacetamidomethyl (PAM)-polystyrene/divinylbenzene resin (Applied Biosystems, Inc. Foster City, Calif.) by the Merrifield solid phase method using an Applied Biosystems 430A automatic synthesizer. The amino acids are coupled in the form of a symmetrical anhydride with the exception of glutamine and asparagine, which react in the form of hydroxybenzotriazole (HOBT) esters. The amino acids used are obtained from Novabiochem (Laüflerlfingen, Switzerland) or from BACHEM (Bubendorf, Switzerland).

The chemical synthesis of the peptides was carried out using a double coupling procedure with N-methylpyrrolidone (NMP) as solvent. The peptides were simultaneously cut from their resin and the side protections using hydrofluoric acid (HF) in an appropriate apparatus (type I HF cutting apparatus, Peptide Institute, Osaka, Japan).

10 ml of HF, 1 ml of anisole and 1 ml of dimethyl sulfide (DMS) are used per 1 g of peptidyl resin and the mixture is stirred for 45 minutes at −2° C. The HF is then evaporated under vacuum. After thorough washing with ether, the peptide is eluted from the resin using 10% acetic acid and then concentrated acetic acid. After dilution with water, the peptide is lyophilized.

The peptides are purified by preparative high performance liquid chromatography on a VYDAC column of type C18 (250×21 mm) (The Separation Group, Hesperia, Calif., U.S.A.). The elution is effected using an acetonitrile gradient at a flow rate of 22 ml/min. The fractions collected are checked by elution under isocratic conditions on a VYDAC C18 analytical column (250×4.6 mm) at a flow rate of 1 ml/min. The fractions which have the same retention time are combined and lyophilized. The major fraction is then analyzed by analytical HPLC using the system described above. The peptide which is considered to be of acceptable purity is reflected by a single peak representing at least 95% of the chromatogram.

The purified peptides are then analyzed with the aim of checking their amino acid composition. They are firstly hydrolyzed in 6 N HCl (Pierce), to which phenol has been added (1% final), at 110° C. for 24 h under vacuum in a Picotag hydrolysis unit (WATERS, Millipore Corporation, Milford USA). Analysis of the amino acids is then carried out using a BECKMAN 6300 amino acid analyzer. The (mean) chemical molecular mass of the peptides is determined using L.S.I.M.S. mass spectrometry in positive ion mode on a VG. ZAB.ZSEQ twin focus instrument connected to a DEC-VAX 2000 collection system (VG analytical Ltd, Manchester, GB).

TABLE 2

| Peptide | Sequence | Theoretical mass | Actual mass | Retention time (*) |
|---------|----------|------------------|-------------|--------------------|
| G28K | KGSKGSKGSKGSKGSKSGSKGSKGSKGSKGG | 2712.04 | 2712.2 | 7.68 min |
| K20R | KIEPLGVAPTKAKRRWQREKR (SEQ ID NO. 1) | 2561.1 | 2560.7 | 17.98 min |

TABLE 2-continued

| Peptide | Sequence | Theoretical mass | Actual mass | Retention time (*) |
|---|---|---|---|---|

(*)HPLC (high pressure liquid chromatography) conditions on a VYDAC 218 TP 52 column (25 cm × 2.1 mm) under the following conditions:
flow rate = 0.25 ml/min,
gradient from 0 → to 100% B' in 30 min with
- buffer A' = water + 0.1% TFA (trifluoroacetic acid)
- buffer B' = 80% $CH_3CN$, 0.1% TFA

EXAMPLE 4

Coupling of a Phosphoramidite Ligand

The coupling of a phosphoramidite ligand to an oligonucleotide is carried out in accordance with the following general procedure:

An oligonucleotide is synthesized on an APPLIED 381 A automatic apparatus from APPLIED BIOSYSTEMS using phosphoramidite chemistry in accordance with the procedure specified by the manufacturer. The phosphoramidite ligand dissolved in anhydrous acetonitrile in a concentration of 0.2M is placed in position X of the synthesizer and the addition of the ligand takes place at the 5' end of the oligonucleotide in accordance with the standard procedure for automatic synthesis when the synthesis of the oligonucleotide is complete.

In the case where the ligand carries a dimethoxytrityl protective group, such as in the case of compounds 1 and 9 to 12 described above, it is necessary to carry out a supplementary step for deprotection of the trityl group by trichloroacetic acid at the end of synthesis. After deprotection, one night at 55° C. in 33% $NH_4OH$ and precipitation from ethanol at −20° C., the oligonucleotide is dried under vacuum and taken up in 1 ml of water.

In the case of compounds referenced 6 and 7, a supplementary step for cleavage of the monomethoxytrityl group is carried out in accordance with the procedure specified by the manufacturer (CLONTECH) after deprotection.

In the case of compounds 11 and 12, coupling is carried out in accordance with the general procedure described above up to the deprotection step, but the ligand is grafted on the terminal base at the 5' end of the oligonucleotide.

It should also be noted that ligands 1, 10, 11 and 12 may undergo addition to themselves via the hydroxyl group liberated by detritylation.

In the case of the compound carrying reference 13, the automatic synthesis is initiated by silica grafted with the ligand, in the standard procedure. The ligand and oligonucleotide coupling takes place via the 3' end of the latter.

It is within the knowledge of a person skilled in the art to produce the silica support with ligands which are suitably protected for the automatic synthesis or are capable of being deprotected as explained above.

In all cases, the oligonucleotides modified at their 5' or 3' ends are purified by inverse phase high pressure liquid chromatography on a Brownlee RP18 column (10 mm–25 cm), producing a gradient of 10 to 35% of buffer B" in the course of 30 minutes and then of 35 to 100% of buffer B" in the course of 3 minutes: the characteristics of buffers A" and B" are as follows:

Buffer A"=0.1M TEAA (triethylammonium acetate), pH=7.0
Buffer B"=50% A+50% $CH_3CN$

EXAMPLE 5

Coupling of a Thiophosphate Ligand to an Oligonucleotide

A 0.2M solution of compound 9b in $CH_3CN$ is added, as described above in Example 4, to the 5' end of an oligonucleotide omitting the oxidation step by the $I_2$, $H_2O$, THF and pyridine mixture.

The cassette containing the silica grafted with the oligonucleotide is brought into contact for 1 hour with a 5% solution of sulfur in a mixture of $CS_2$/pyridine in proportions of 50/50 respectively.

After rinsing carefully with the $CS_2$/pyridine mixture, deprotection is carried out as described above.

Table 3 below illustrates the products obtained after coupling of the compounds 1 to 13 described above to any oligonucleotide and deprotection, and also gives a naked oligonucleotide by way of reference.

TABLE 3

| by coupling with x | ligand X |
|---|---|
| 3'oligonucleotide5'.OH | — |
| 3'oligonucleotide5'-O−P(=O)(O−)−O−(CH$_2$)$_8$−OH | 1 |
| 3'oligonucleotide5'-O−P(=O)(O−)−O−(CH$_2$)$_2$−O−CH$_2$−C$_6$H$_5$ | 2 |
| 3'oligonucleotide5'-O−P(=O)(O−)−O−(CH$_2$)$_6$−C$_6$H$_5$ | 3 |
| 3'oligonucleotide5'-O−P(=O)(O−)−O−(CH$_2$)$_5$−CH$_3$ | 4 |
| 3'oligonucleotide5'-O−P(=O)(O−)−O−(CH$_2$)$_6$−NH$_2$ | 5 |
| 3'oligonucleotide5'-O−P(=O)(O−)−O−(CH$_2$)$_{12}$−NH$_2$ | 6 |
| 3'oligonucleotide5'-O−P(=O)(O−)−O−(CH$_2$)$_3$−NH$_2$ | 7 |
| 3'oligonucleotide5'-O−P(=O)(O−)−O−(CH$_2$)$_6$−S−CPh$_3$ | 8 |
| 3'oligonucleotide5'-O−P(=O)(O−)−O− | 9a |
| 3'oligonucleotide5'-O−P(=O)(O−)−S− | 9b |
| 3'oligonucleotide5'-O−P(=O)(O−)−O−CH$_2$−CH(CH$_2$−NH$_2$)(CH$_2$−OH) | 10 |
| 3'oligonucleotide5'-O − (thymidine-5-acrylamide derivative with NH−(CH$_2$)$_6$−NH$_2$) | 11 |

TABLE 3-continued

| by coupling with x | ligand X |
|---|---|
| 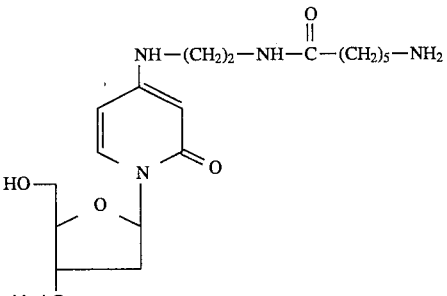 | 12 |
| HO—CH₂—CH—CH₂—O-3'oligonucleotide₅'-OH<br>          \|<br>          CH₂—NH₂ | 13 |

EXAMPLE 6

Coupling of a Peptide Ligand to an Oligonucleotide

The coupling of a peptide to an oligonucleotide may be carried out in accordance with the known methods known as direct or indirect methods. A direct method is understood to be coupling by automatic synthesis as described in the publication by C. D. Juby, Tetrahedron Lett., 879 (1991) and the method according to which an oligonucleotide having a reactive group at its 5' or 3' end or on a base is synthesized. The oligonucleotide is subjected to a deprotection step and coupled with a peptide, prepared beforehand, by formation of a covalent bond between two complementary reactive groups, one carried by the oligonucleotide and the other by the peptide. For example, it is possible to couple primary amines with an activated carboxylic acid or an aldehyde or, alternatively, a thiol group with a halogenoalkyl. An indirect coupling method signifies that the oligonucleotide and the peptide each carry a reactive group, which groups may be identical or different from one another and said 2 groups not being complementary. Consequently, it is necessary to use an intermediate coupling agent, which may be homobifunctional if the two groups are identical or heterobifunctional if the two groups are different. Amongst the homobifunctional coupling agents, the following may be mentioned: DITC (phenylene 1,4diisothiocyanate), if the two reactive groups are primary amine groups, DSS (disuccinimidyl suberate) or the like. Amongst the heterobifunctional coupling agents, the following may be mentioned: SMCC (succinimidyl 4-(N-maleimidomethyl)cyclohexane-1-carboxylate), if the two reactive groups each independently of one another have a primary amine group and a thiol group, SMPB (succinimidyl 4-(p-maleimidophenyl)-butyrate) or the like.

According to the invention, the coupling of an oligonucleotide and a peptide was carried out by the indirect technique as described in detail below. However, of course, this is only a non-limiting illustration of a particular embodiment of the invention.

Also, according to the invention, the synthesis of an oligonucleotide with a ligand represented by compound 5 is effected and a purification step is then carried out as described in Example 4. After drying under vacuum, the oligonucleotide (3×10⁻⁸ mol) was taken up in 25 µl of 0.1M sodium borate buffer of pH 9.3. 500 µl were added to 30 mg/ml of DITC (Fluka 78 480) in DMF. The mixture was stirred for about 1 hour 30 min at 37° C. before addition of 3 ml of H₂O.

After extraction of the solution with butanol (3×3 ml), the residual aqueous phase (600 µl) is dried under vacuum and then taken up in 1.5×10⁻⁷ mol of peptides in 300 µl of 0.1M borate buffer of pH 9.3. After reaction overnight at 37° C. with stirring, the conjugated oligopeptide obtained was purified on a Brownlee column RP 300 (4.6×100 mm) under the following conditions:

Two buffers were used, respectively C=0.1M TEAA, pH 8.0, and D=50% C+50% CH₃CN. A gradient of 0 to 30% of C was produced in the course of 30 min and then of 30 to 100% of C in the course of 3 min.

Using the procedures described above, 3 oligonucleotides a, b and c, respectively, were synthesized and were or were not coupled to diverse phosphoramidite, thiophosphate or peptide ligands.

The nucleotide sequence of oligonucleotide a is as follows: 5'-GCATTTAGAGCC-3' (SEQ ID NO. 3).

Oligonucleotide b is represented by the sequence: 5'-TG-CATTTAGAGCC-3' (SEQ ID NO. 4).

Oligonucleotide c is characterized by the sequence: 5'-TCTACGCATTTCACCGCTACAC-3' (SEQ ID NO. 5).

The results are presented in Table 4 below:

TABLE 4

| 5-oligonucleotide-3' | X (ligand) | OLIGO | RETENTION TIME (#) HPLC (minutes) |
|---|---|---|---|
| GCATTTAGAGCC (SEQ ID NO. 3) | — | a | 17.8 |
| X-GCATTTAGAGCC (SEQ ID NO. 3) | 5 | a-5 | 16.0 |
| X-GCATTTAGAGCC (SEQ ID NO. 3) | 6 | a-6 | 28.9 |
| X-GCATTTAGAGCC (SEQ ID NO. 3) | 8 | a-8 | 35.0 |

TABLE 4-continued

| 5-oligonucleotide-3' | X (ligand) | OLIGO | RETENTION TIME (#) HPLC (minutes) |
|---|---|---|---|
| TGCATTTAGAGCC (SEQ ID NO. 4) | — | b | 27.8 |
| X-TGCATTTAGAGCC (SEQ ID NO. 4) | 1 | b-1 | 24.3 |
| XX-TGCATTTAGAGCC (SEQ ID NO. 4) | 1 | b-1*2 | 32.1 |
| XXX-TGCATTTAGAGCC (SEQ ID NO. 4) | 1 | b-1*3 | 34.5 |
| X-TGCATTTAGAGCC (SEQ ID NO. 4) | 2 | b-2 | 23.3 |
| X-TGCATTTAGAGCC (SEQ ID NO. 4) | 3 | b-3 | 35.0 |
| X-TGCATTTAGAGCC (SEQ ID NO. 4) | 4 | b-4 | 26.2 |
| X-TGCATTTAGAGCC (SEQ ID NO. 4) | 5 | b-5 | 17.0 |
| X-TGCATTTAGAGCC (SEQ ID NO. 4) | 6 | b-6 | 32.3 |
| X-TGCATTTAGAGCC (SEQ ID NO. 4) | 7 | b-7 | 16.5 |
| X-TGCATTTAGAGCC (SEQ ID NO. 4) | 8 | b-8 | 33.8 |
| X-TGCATTTAGAGCC (SEQ ID NO. 4) | 9a | b-9a | 17.3 |
| X-TGCATTTAGAGCC (SEQ ID NO. 4) | 9b | b-9b | 16.4 |
| X-TGCATTTAGAGCC (SEQ ID NO. 4) | 10 | b-10 | 17.2 |
| X-TGCATTTAGAGCC (SEQ ID NO. 4) | 11 | b-11 | 17.3 |
| X-TGCATTTAGAGCC (SEQ ID NO. 4) | 12 | b-12 | 18.2 |
| TGCATTTAGAGCC-X (SEQ ID NO. 4) | 13 | b-13 | 17.0 |
| TCTACGCATTTCACCGCTACAC (SEQ ID NO. 5) | — | c | 17.5 |
| X-TCTACGCATTTCACOGCTACAC (SEQ ID NO. 5) | 1 | c-1 | 24.3 |
| XXX-TCTACGCATTTCACOGCTACAC (SEQ ID NO. 5) | 1 | c-1*3 | 33.5 |
| X-TCTACGCATTTCACOGCTACAC (SEQ ID NO. 5) | 5 | c-5 | 17.1 |
| X9-TCTACGCATTTCACOGCTACAC (SEQ ID NO. 5) | 10 | c-10*9 | 19.5 |
| X9-TCTACGCATTTCACOGCTACAC (SEQ ID NO. 5) | 11 | c-11*9 | 19.2 |

TABLE 5

| 5'-oligonucleotide-3' | PEPTIDE | ABBREVIATED NAME | RETENTION TIME HPLC (minutes) | RATIO |
|---|---|---|---|---|
| TGCATTTAGAGCC (SEQ ID NO. 3) | G28K | b-G28K | 25.7 | 1.0 |
| GCATTTAGAGCC (SEQ ID NO. 4) | G28K | a-G28K | 24.8 | 1.0 |
| TGCATTTAGAGCC (SEQ ID NO. 5) | K20R | b-K20R | 36.1 | 1.1 |
| TCTACGCATTTCACCGCTACAC (SEQ ID NO. 6) | K20R | c-K20R | 39.3 | 0.9 | in which X characterizes the ligand in accordance with the nomenclature used above; the symbol *n, n representing the number 2, 3 or 9, signifies that the ligand may add to itself n times.

The symbol - in the X column of Table 4 signifies that the oligonucleotide is synthesized without a ligand.

The symbol # signifies that the chromatography conditions are those described for Example 4.

In Table 5, the oligonucleotide is quantified in picomoles by UV measuring the absorbance at 260 nm, in accordance with the Applied Biosystems procedure. The peptide is quantified in picomoles by analysis of the amino acids in accordance with the method described in Example 3. The oligo/peptide ratio is the ratio of these two values.

EXAMPLE 7

Detection of a Nucleic Acid Fragment by the Technique known as the "sandwich" Technique 100 µl of a solution of a capture oligonucleotide, which is unmodified or modified with a ligand, in a concentration of 0.15 µM in PBS 3X (0.45M NaCl; 0.15 M sodium phosphate; pH 7.0) are introduced into a polystyrene microtitration plate (Nunc 439454). The plate is incubated for two hours at about 37° C. and then washed 3 times with 300 µl of PBS Tween (polysorbate) (0.15M NaCl; 0.05M sodium phosphate; pH 7.0; 0.5% Tween (polysorbate) 20 (MERCK 822184)).

50 µl of a target sequence in various concentrations in PBS salmon buffer (PBS 3X+10 mg/ml salmon sperm DNA (Sigma D9156)) are added to the wells, followed by 50 µl of a solution of an oligonucleotide-peroxidase conjugate in an oligonucleotide concentration of 0.1 ng/µl (15 nM) in a PBS-horse buffer (PBS 3X+10% of horse serum (BIOMERIEUX 55842)).

The plate is incubated for 1 hour at 37° C. and washed with 3 times 300 µl of PBS Tween (polysorbate).

100 µl of OPD (ortho-phenylenediamine, Cambridge Medical Biotechnology ref. 456) substrate in an OPD buffer (0.05M citric acid; 0.1M $NaH_2PO_4$; pH 4.93) having a concentration of 4 mg/ml, to which 30 volume $H_2O_2$ is added at the time of use to 1/1000, are added per well. After a reaction time of 20 minutes, the enzymatic activity is blocked by 100 µl of 1N $H_2SO_4$. The reading is carried out on an AXIA Micro Reader (BIOMERIEUX) at 492 nm.

EXAMPLE 8

In accordance with the general procedure described in Example 7, a target nucleic acid fragment determined by the sequence 5'-AAGGTCAACCGGAATTTCATTTTGGGGCTCTAAATGCAATACAATGTCTTG
CAATGTTGCCTTA-3'    (SEQ ID NO. 6)

was detected, at a concentration of $10^{-9}$M and of $10^{-10}$M respectively, using a capture oligonucleotide of sequence 5'-TGCATTTAGAGCC-3'(SEQ ID NO. 4), which was unmodified or modified with a ligand, and a detection oligonucleotide conjugated to peroxidase of sequence 5'-TAAGGCAACATTGCAAGATA-3'(SEQ ID NO. 7).

Figure 2:
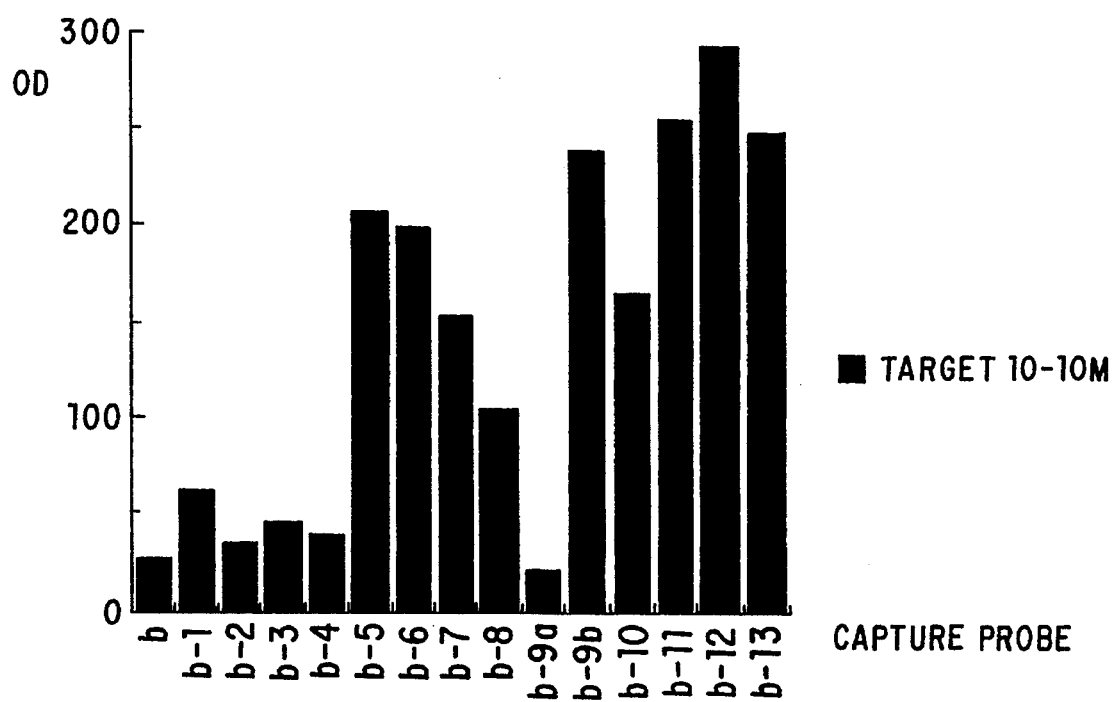
FIG. 2 shows further capture oligonucleotides as defined in Tables 4 and 5.

The results are presented in FIGS. 1 and 2, in which figures the capture oligonucleotides are designated in accordance with the rules defined above in Tables 4 and 5.

The effect of the addition of a ligand to the end of an oligonucleotide on the efficiency of the detection may be quantified by the oligonucleotide-ligand signal/naked oligonucleotide signal ratio. A naked oligonucleotide is understood to be an oligonucleotide synthesized in the standard manner, that is to say 3' OH, 5' OH and not possessing a ligand on the bases.

The oligonucleotide-ligand signal/naked oligonucleotide signal ratio is shown in the table below, in which X represents a ligand in accordance with the terminology used above and b represents an oligonucleotide as determined above.

TABLE 6

| X | 1 | 2 | 3 | 4 | 5 | 6 | 7 | 8 |
|---|---|---|---|---|---|---|---|---|
| Ratio b-X/b | 2.6 | 1.3 | 1.5 | 1.2 | 8.2 | 7.8 | 6.3 | 3.8 |
| X | 9a | 9b | 10 | 11 | 12 | 13 | G28K | K20R |
| Ratio b-X/b | 0.5 | 6.7 | 7.1 | 9.7 | 11.1 | 6.8 | >12.6 | >12.6 |

This table shows that the addition of a ligand to an oligonucleotide permits a significant increase in the signal, this increase being up to more than 10-fold in some cases. Not all of the ligands have the same effect and the presence of a primary amine is a determining factor. This is also confirmed by FIGS. 1 and 2 (giving the results obtained (OD (optical density) data) with diverse capture probes).

As can be seen from FIGS. 1 and 2, the concentration of the target has no effect.

With ligands 5, 6, 7, 10 and 13, which contain a primary amine on a straight-chain or branched alkyl chain, the ratio b-X/b is between 6.3 and 8.2, whereas for ligands 1, 2, 3, 4 and 9, which do not contain primary amines, this ratio is between 1.2 and 3.7.

In the case of ligand 9a, which introduces a phosphate group, the effect is negative, with a ratio of 0.5.

If the amino ligand is carried by an aliphatic chain grafted on the base of an oligonucleotide which is not complementary to the target, the same effect of increasing the signal is visible, which is the case with ligands 11 and 12.

EXAMPLE 9

The general procedure described in Example 7 is repeated, using simple ligands, ligands which are capable of adding onto themselves, peptide ligands and a thymine (T) nucleotide. The capture oligonucleotide b is characterized by the sequence 5'-TGCATTTAGAGCC-3' (SEQ ID NO. 4).

Figure 3:
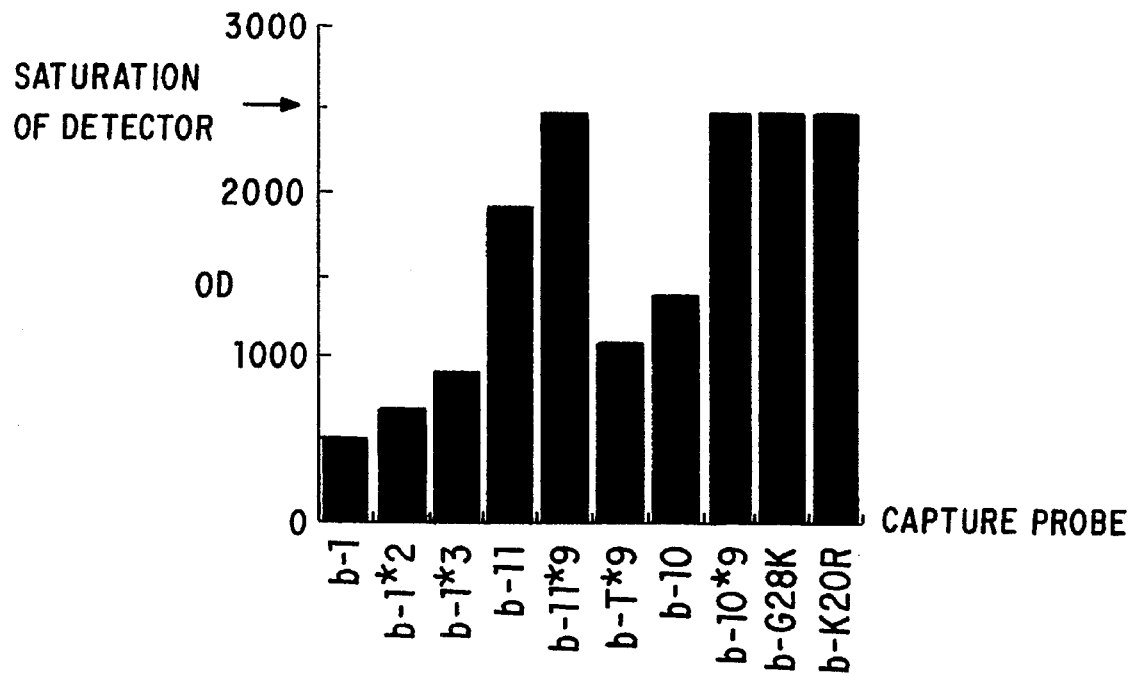
FIG. 3 shows capture oligonucleotide b.

The results are presented in FIG. 3 and in Table 7.

TABLE 7

| X | 1 | 1*2 | 1*3 | 11 | 11*9 | T*9 | 10 | 10*9 | G28K | K20R |
|---|---|-----|-----|----|------|-----|----|------|------|------|
| Ratio b-X/b | 2.6 | 3.4 | 4.6 | 9.7 | >12.6 | 4.4 | 7.1 | >12.6 | >12.6 | >12.6 |

As can be seen from this figure and from Table 7, in which X represents the ligand, the symbol *n signifies the ligand capable of adding onto itself n times and b represents the capture oligonucleotide.

The detection sensitivity is increased by multiple addition of the ligand, whatever the type of ligand, but with a very pronounced effect when the ligand carries an amine group. This effect of the amine group is confirmed by comparison between ligand 1 ($(CH_2)_8$-OH) and ligand 5 ($(CH_2)_6$-$NH_2$) of the preceding example. In fact, ligand 1, which carries a hydroxyl group, even when added to itself 3 times, gives an improvement of only 4.56, whereas ligand 5, which carries a primary amine group, produces an improvement of 8.20. Similarly, for the thymine (T) ligand added to itself 9 times, the improvement in sensitivity is only 4.4, in comparison with ligand 11 added to itself 9 times, which gives an improvement in sensitivity of 12.6. Ligand 11 differs from the thymine ligand in respect of the presence of an aliphatic arm containing a primary amine on the T base in position 5.

EXAMPLE 10

The same general procedure as that described in Example 7 is used. A short capture probe, referenced a, which has the sequence 5'-GCATTTAGAGCC-3' (SEQ ID NO. 3) and which is one base shorter than the probe b previously tested is used. The ligands coupled to the capture probe are, respectively, the phosphoramidite ligands 5 and 6 and the peptide ligand G28K.

The target is deposited in a concentration of $10^{-10}$M.

Figure 4:
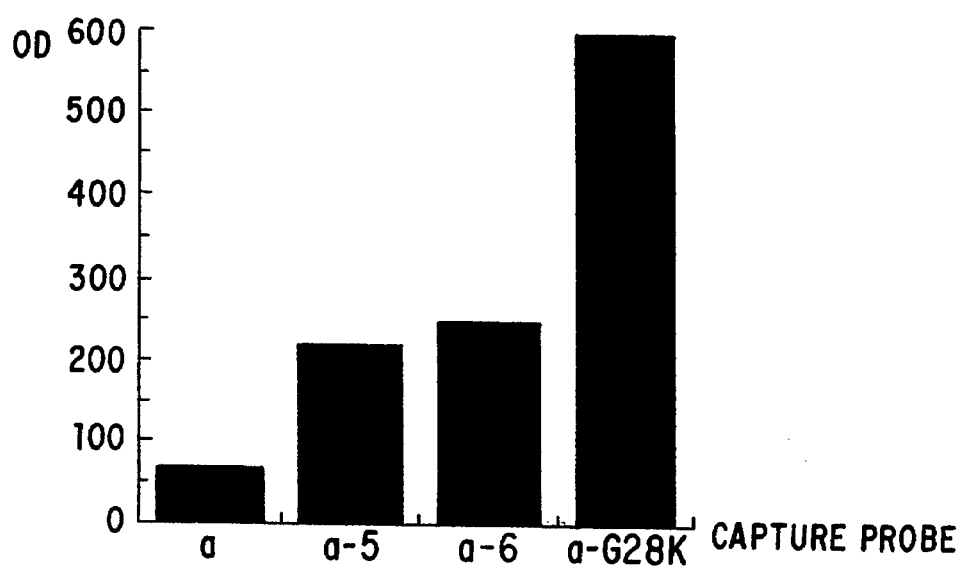
FIG. 4 shows increase in detection sensitivity of a probe by the presence of a ligand carrying an amine group.

As can be seen from FIG. 4, the detection sensitivity is increased in the presence of a ligand which carries a primary amine group, compared with a naked oligonucleotide. Moreover, it is found that the detection sensitivity is substantially increased in the presence of a peptide ligand, compared with a phosphoramidite ligand 5 and 6. The results are confirmed in Table 8 below, in which X represents the ligand and a respresents the oligonucleotide.

TABLE 8

| X | 5 | 6 | G28K |
|---|---|---|------|
| Ratio a-X/a | 3.2 | 3.7 | 8.9 |

EXAMPLE 11

A detection procedure identical to that described in Example 7 is used. The capture oligonucleotide is oligonucleotide c which has the sequence 5'-TCTACG-CATTTCACCGCTACAC-3' (SEQ ID NO. 5) and is modified at the 5' end with a ligand and which is deposited in a concentration of 0.30 µM. The target consists of $5\times10^9$ moles of a mixture of RNA 16S and 23S E. coli (marketed by BOEHRINGER under the reference 206938) in 50 µl of a PBS salmon buffer. The detection probe coupled to peroxidase has the sequence 5'-TCTAATCCTGTTTGCTCCC-3' (SEQ ID NO. 8).

Figure 5:
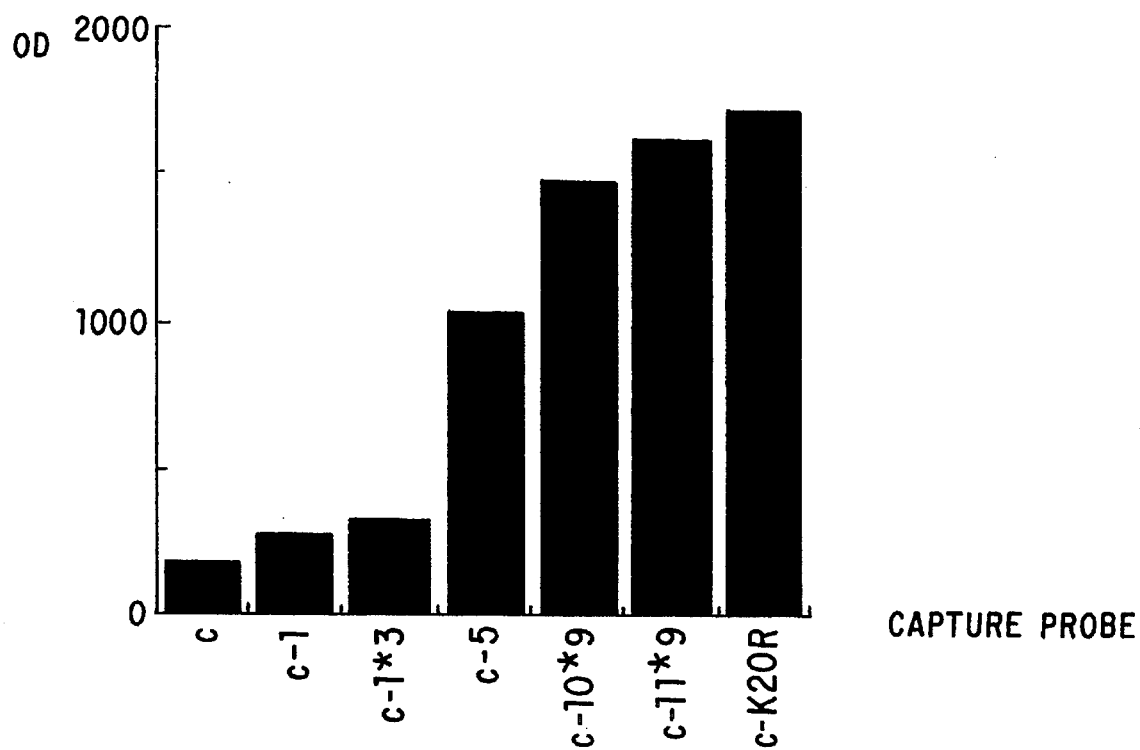
FIG. 5 shows the detection sensitivity of a probe is increased by the presence of a ligand.

As shown in FIG. 5, the detection sensitivity is increased by the presence of a ligand and this increase is the greater when a ligand coupled several times to itself is used.

The results are confirmed in Table 9 below, in which X represents the ligand and c the capture oligonucleotide.

TABLE 9

| X | 1 | 1*3 | 5 | 10*9 | 11*9 | K20R |
|---|---|-----|---|------|------|------|
| Ratio c-X/c | 1.5 | 1.8 | 5.7 | 8.2 | 9.1 | 9.6 |

It is also found that with a 22-base capture probe, ligands 10 and 11 added 9 times to themselves and the peptide ligand K20R have substantially the same effect.

EXAMPLE 12

The same procedure as that described in Example 7 is used. The nature of the buffer for dilution of the capture oligonucleotide modified with chemical ligands is varied. The capture oligonucleotide is oligo b as described above, prepared as a 0.15 µM solution in, respectively, buffers A*, B*, C* and D*. The target S described in Example 8 is deposited in a concentration of $10^{-10}$M.

A*=150 mM sodium phosphate, pH 7.0; 450 mM NaCl
B*=150 mM sodium phosphate; pH 4.2; 450 mM NaCl
C*=150 mM sodium phosphate; pH 8.5; 450 mM NaCl
D*=150 mM Tris, pH 7.0; 450 mM NaCl.

Figure 6:
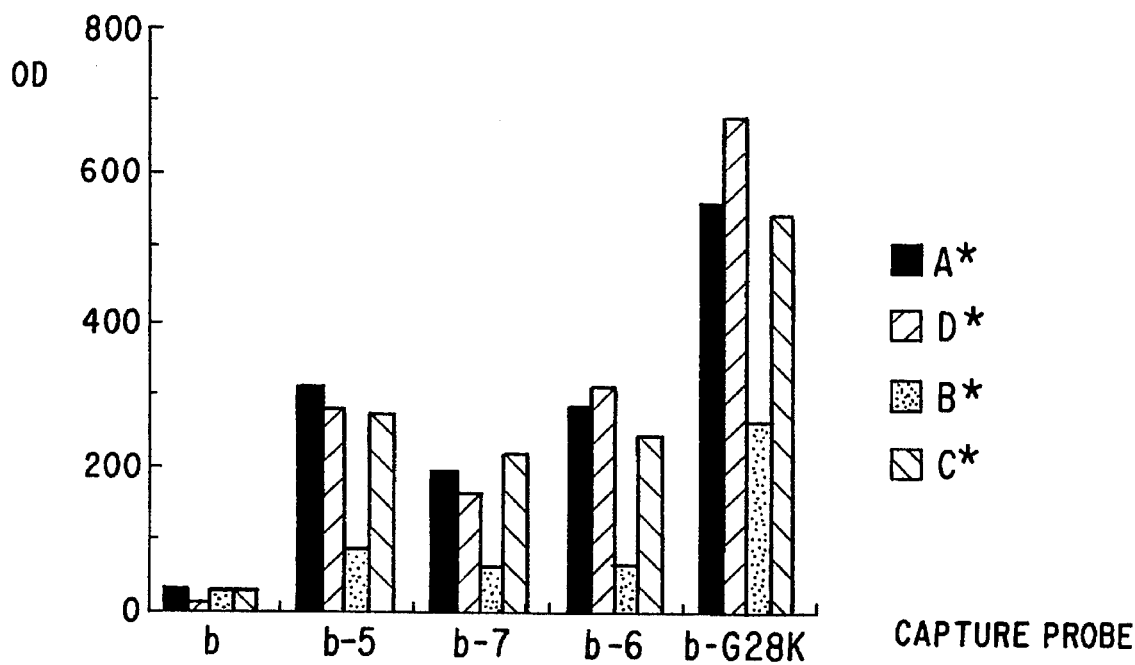
FIG. 6 shows the effect of pH on detection sensitivity of a probe.

As can be seen from FIG. 6, whatever the buffer, the effect of the ligand on the detection sensitivity is retained. This effect is reduced at acid pH with buffer B*.

EXAMPLE 13

The effect of the ligand on the specificity will now be shown. A sandwich procedure identical to that described in Example 7 and 2 DNA fragments in a concentration of $10^{-10}$M as target are used. The sequence S below is perfectly homologous to the capture oligonucleotide b, which is unmodified or modified with ligand.

The sequence SGT described below contains a mispairing of GT type in the middle of the complementary region of the capture probe.

Sequence S =
3'-ATTCCGTTGTAACGTTCTGTAACATAACGTAAATCTCGGGGTTTTACTTTAAGGCCA
    ACTGAA-5'   (SEQ ID NO. 9)

Sequence SGT =
3'-ATTCCGTTGTAACGTTCTGTAACATAACGTAAGTCTCGGGGTTTTACTTTAAGGCCA
    ACTGAA-5'   (SEQ ID NO. 10)

The improvement in the signal which is afforded by the presence of a ligand must not reduce the specificity of the detection. The S signal/SGT signal ratio may therefore serve as reference to determine the system performance.

Figure 7:
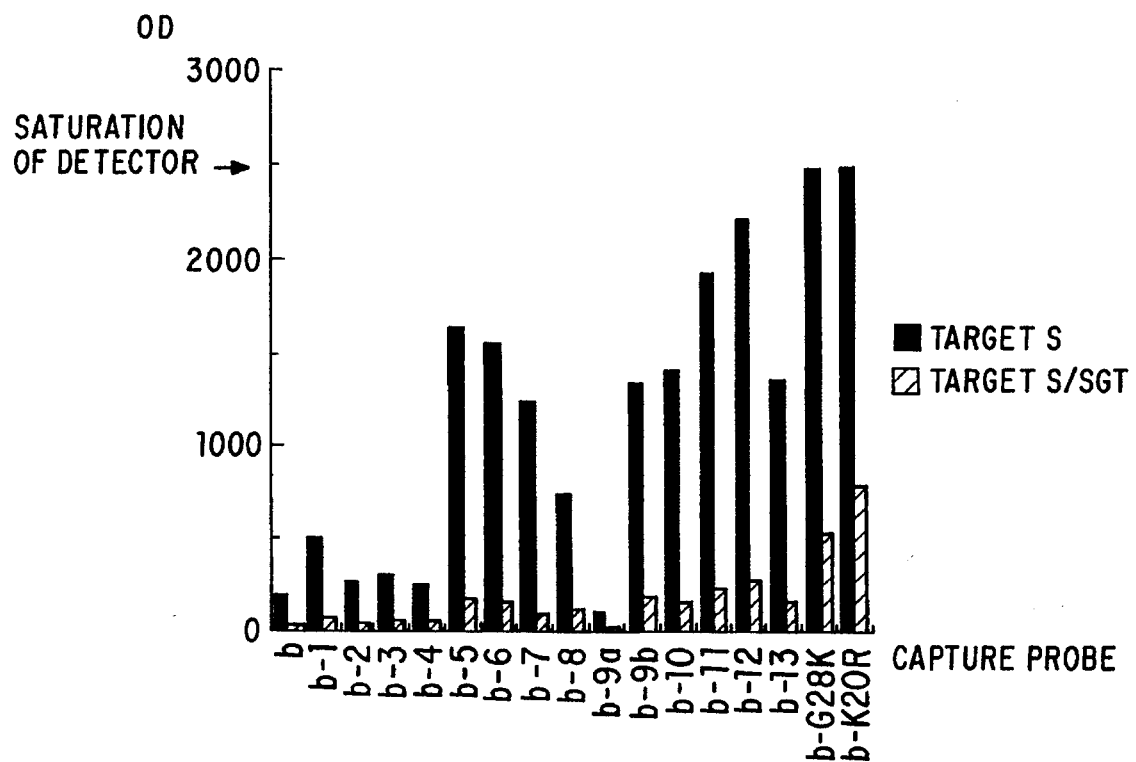
FIG. 7 shows that improvement in the detection signal of a probe should not adversely affect specificity of detection.

The results are presented in FIG. 7 and in Table 10 below, in which b represents the capture oligonucleotide and X the ligand.

TABLE 10

| b-X | b | b-1 | b-2 | b-3 | b-4 | b-5 | b-6 | b-7 |
|-----|---|-----|-----|-----|-----|-----|-----|-----|
| TARGET/MODIFIED TARGET | 7.1 | 7.8 | 9.1 | 8.2 | 8.2 | 9.5 | 9.9 | 15.3 |

| b-X | b-8 | b-9b | 10 | 11 | 12 | 13 | G28K | K20R |
|-----|-----|------|----|----|----|----|------|------|
| TARGET/MODIFIED TARGET | 6.8 | 7.3 | 8.9 | 7.9 | 7.9 | 8.6 | >4.7 | >3.2 |

It is found that the improvement in the signal which is afforded by the ligand in no way reduces the specificity of the detection. In the case of the use of peptide ligands, a reduction in the signal improvement is observed, compared with that obtained with phosphoramidite ligands, and this is due to saturation of the detector. In fact, the specificity of the detection is not changed by the use of the peptide ligand.

EXAMPLE 14

The detection of a nucleic acid fragment is carried out on a VIDAS automated unit (registered trademark— marketed by BIOMERIEUX SA - VITEK). The detection is carried out with the aid of an SPR conical support (marketed by VITEK (USA), trademark) produced from a material sold under the name K resin (which is a butadiene-styrene copolymer) and a strip. The sandwich hybridization reaction described in the procedure below takes place on the inner wall of the cone.

Oligonucleotides, which are unmodified or modified with a ligand, are passively fixed on the internal surface of the SPR cone in a concentration of 0.15 µM in a volume of 315 µl of a PBS 4X solution (200 mM sodium phosphate, pH 7.0, 600mM NaCl). After a night at ambient temperature or two hours at 37° C., the cones are washed twice with a PBS Tween (polysorbate) solution and then dried under vacuum. The strip contains all of the reagents necessary for the detection, that is to say:

200 µl of a 15 nM solution of an oligonucleotide having the sequence 5'-TAAGGCAACATTGCAAGATA-3' (SEQ ID NO. 7), coupled at the 5' end to alkaline phosphatase, 3 times 600 µl of PBS Tween (polysorbate) wash solution and a substrate cell.

200 µl of the target in a concentration of $10^{-9}$M in the same buffer as in Example 7 are placed in the first well of the strip.

After incubating the cone for 30 minutes with the target plus detection probe mixture, the cone is washed 3 times with a PBS Tween polysorbate solution. 250 µl of MUP (4-methylumbelliferyl phosphate) substrate in solution in a diethanolamine buffer are aspirated into the cone and then released into a reading cell. The apparatus measures the fluorescent signal expressed in RFU (relative fluorescence units) of the cell.

Figure 8:
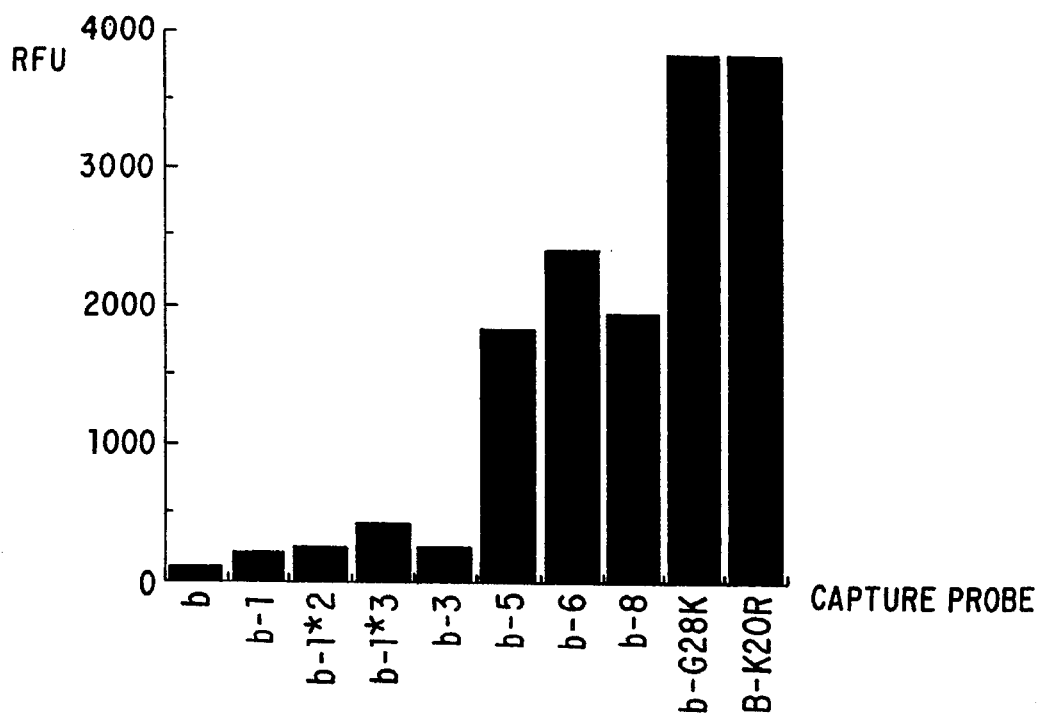
FIG. 8 shows the results of the procedure carried out in Example 14.

The results are shown in FIG. 8 and in Table 11 below, in which X represents the ligand, *n signifies addition of the ligand to itself n-times and b represents the capture oligonucleotide as represented above.

TABLE 11

| X | 1 | 1*2 | 1*3 | 3 | 5 | 6 | 8 | G28K | K20R |
|---|---|-----|-----|---|---|---|---|------|------|
| Ratio b-X/b | 2.3 | 2.8 | 4.8 | 2.7 | 20.4 | 26.9 | 21.6 | >43 | >43 |

The results confirm the effect of the ligand in improving the detection sensitivity and the dominant role of ligands carrying at least one primary amine functional group.

EXAMPLE 15

The detection of a nucleic acid sequence is carried out in accordance with the sandwich procedure as described in Example 7, using irradiated or non-irradiated polystyrene plates marketed by NUNC under the references 439454 and 269620 respectively.

The target acid fragment is a DNA fragment of the papilloma virus of type 16 (region E7) used in a concentration of $10^{-10}$M.

The sequence of the capture oligonucleotide used, referenced d, is: 5'-GACAACTGATCTCTAC-3' (SEQ ID NO. 11).

The sequence of the detection oligonucleotide, coupled at the 5' end to alkaline phosphatase, is: 5'-CCGGACAGAGC-CCATTAC-3' (SEQ ID NO. 12).

The results are presented in Tables 12 and 13 below.

TABLE 12

| OLIGO-LIGAND | NON-IRRADIATED PLATE | IRRADIATED PLATE |
|---|---|---|
| d | 0.100 OD | 0.230 OD. |
| d-5 | 0.180 OD | 0.490 OD. |

TABLE 13

| OLIGO-LIGAND | IRRADIATED/NON-IRRADIATED SIGNAL RATIO |
|---|---|
| d | 2.3 |
| d-5 | 2.7 |

The above results confirm the dominant role of the ligand in the detection sensitivity. Moreover, an improvement in the detection sensitivity is found when irradiated microtitration plates are used.

EXAMPLE 16

The detection of a nucleic acid sequence is carried out in accordance with the sandwich procedure on the VIDAS automated unit in accordance with the procedure described in Example 14, using irradiated or, respectively, non-irradiated K resin cones. These cones are marketed by VITEK SYSTEM.

The DNA and the capture and detection oligonucleotides used are identical to those described in Example 15. The ligand used is that referred to above in Example 5.

The results are presented in Table 14 below.

TABLE 14

| OLIGO-LIGAND | SPR NON-IRRADIATED | SPR IRRADIATED |
|---|---|---|
| d | 84 RFU | 540 RFU |
| d-5 | 1302 RFU | 3917 RFU |

The activated SPR/non-activated SPR detection ratios are:

| OLIGO-LIGAND | Activated/non-activated RATIO |
|---|---|
| d | 6.43 |
| d-5 | >>3.00 |

The above results again confirm the effect of the ligand on the detection sensitivity. Moreover, a reduction in the improvement in the signal is found when irradiated cones are used, but this is due to a saturation of the detector. The ratio is therefore markedly greater than 3.00 (>>3.00).

EXAMPLE 17

The stability of the cones used at various temperatures is demonstrated below.

In fact, in the case of the use of cones for the VIDAS automated unit, as components of the system for detection of nucleic acid fragments, said cones must be sold ready for use, that is to say with the capture oligonucleotide immobilized. One factor determining their use is their stability over time. Stability experiments have been carried out at three different temperatures: 4°, 20° C. and 37° C. respectively. The results obtained are summarized in Table 15 below after 42 days for each temperature:

TABLE 15

| TEMPERATURE | day 42/day 1 SIGNAL RATIO |
|---|---|
| 4° | 100% |
| 20° | 98% |
| 37° | 86% |

The above results show the excellent stability of the cones used after storing for 42 days in a refrigerator at a temperature of 4° C. Moreover, an increase in the temperature has only very little effect on the stability of the products.

As can be seen from all of the examples described above, the addition of a ligand to a nucleic acid fragment in all cases increases the detection sensitivity. This effect is further increased when a ligand carrying at least one polar functional group, such as an amino group, is used. Moreover, fixation of the ligand to the solid support is very easy since it takes place directly by passive adsorption. The hypothesis put forward to explain the direct passive adsorption of the ligand on the support is the combination of hydrophobic interactions between the hydrophobic part of the ligand and the support and polar interactions between the polar groups of the ligand and polar groups of the support, it being possible for the latter to be provided during the process for polymerization of the support or by means of irradiation of the support after polymerization.

We claim:

1. A process for immobilization by non-covalent attachment to a solid support, of a nucleic acid fragment containing less than 100 nucleotides, comprising: forming a derivative from the covalent coupling of said fragment with a ligand having a molecular mass of less than 5000 and containing at least one amine group, and depositing said derivative on the support, said derivative not being capable of forming a covalent bond with said support under conditions of said depositing, with the proviso that when said ligand is a nucleotide or oligonucleotide it comprises at least one nucleotide modified so as to introduce said amine group.

2. The process as claimed in claim 1, wherein said amine group is chosen from the group consisting of amine, amidino, quanidino, triazinyl, indolyl and imidazolyl groups.

3. The process as claimed in claim 1, wherein said ligand is bonded to a terminal nucleotide of said fragment.

4. The process as claimed in claim 3, wherein said ligand is bonded to the base of said terminal nucleotide.

5. The process as claimed in claim 1, wherein said ligand contains a group chosen from the group consisting of:

the groups of formula (I):

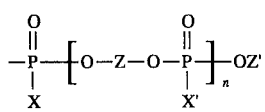

in which n is zero or an integer from 1 to 30, the groups Z are chosen from alkylene or alkenylene groups having 2 to 30 carbon atoms, Z' is an alkyl or alkenyl group having 2 to 30 carbon atoms and X and X' independently represent $-O^-M^+$, $-S^-M^+$ or an alkyl, alkoxy, aryloxy, aminoalkyl or aminoalkoxy group, $M^+$ being an alkali metal cation or $NH_4^+$, with the proviso that at least one of the groups Z and Z' is substituted by an amine group or by a group carrying an amine group;

the groups of formula (II):

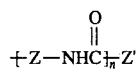

in which n, Z and Z' are defined as above, and the groups of formula (III):

   (III)

in which L is a peptidyl radical comprising at leash one unit derived from a member of the group consisting of lysine, arginine, ornithine, glutamine, asparagine, serine, threonine, tyrosine, histidine and tryptophan containing a side chain substituted by an amine group.

6. The process as claimed in claim 5, wherein said ligand corresponds to the formula (I), n being zero or an integer from 1 to 10, Z is an alkylene having from 2 to 12 carbon atoms and Z' is an alkyl having from 2 to 12 carbon atoms, at least one of the groups Z and Z' being substituted by at least one amine, hydroxyl or hydrazino group.

7. The process as claimed in claim 5, wherein n= 0 and X represents $O^-M^+$.

8. The process as claimed in claim 6, wherein said ligand corresponds to the formula (II) where n=0 and Z' represents an alkyl group having 3 to 12 carbon atoms, substituted by at least one amine group.

9. The process as claimed in claim 8, wherein said alkyl group is also substituted by at least one hydroxyl group.

10. The process as claimed in claim 5, wherein said ligand corresponds to the formula (II) where n=1, Z represents an alkylene or alkenylene having at least 2 carbon atoms and Z' represents an alkyl group substituted by at least one amine group.

11. The process as claimed in claim 5, wherein said ligand corresponds to the formula (II), where n=0.

12. The process as claimed in claim 5, wherein —L is chosen from:

(KGS)$_m$-KGG, m being an integer which may vary from 1 to 15, and

KIEPLGVAPTKAKRRWQREKR (SEQ ID NO. 1).

13. The process as claimed in claim 12, wherein said support comprises a member of the group consisting of a polystyrene polymer, a butadiene-styrene copolymer, a styrene-acrylonitrile copolymer, a styrene-methyl methacrylate copolymer, a polypropylene, a polycarbonate and mixtures thereof.

14. The process as claimed in claim 1, wherein said immobilized fragment contains less than 50 nucleotides.

15. A support on which a nucleotide sequence is immobilized, wherein said support is obtained by the process of claim 1.

16. The process as claimed in claim 14, wherein said immobilized fragment contains less than 30 nucleotides.

17. The process of claim 1, wherein said amine group is a primary amine group.

18. The process of claim 1, wherein said solid support is hydrophobic.

19. The process of claim 1, wherein said solid support comprises at least one of polystyrene polymer and a styrene-based copolymer.

20. The process of claim 19, wherein the solid support comprises a mixture of a butadiene-styrene copolymer and one or more polymers or copolymers selected from the group consisting of polystyrene, styrene/acrylonitrile copolymers, styrene/methyl methacrylate copolymers, polypropylene and polycarbonate.

* * * * *